(12) United States Patent
Tomoe et al.

(10) Patent No.: US 8,979,366 B2
(45) Date of Patent: Mar. 17, 2015

(54) X-RAY PHOTOGRAPHING DEVICE

(75) Inventors: Takeshi Tomoe, Tokyo (JP); Takanori Wagatsuma, Tokyo (JP); Terumi Takemoto, Tokyo (JP)

(73) Assignee: The Yoshida Dental Mfg. Co., Ltd., Sumida-ku, Tokyo (JP)

( * ) Notice: Subject to any disclaimer, the term of this patent is extended or adjusted under 35 U.S.C. 154(b) by 182 days.

(21) Appl. No.: 13/816,219

(22) PCT Filed: Aug. 9, 2010

(86) PCT No.: PCT/JP2010/063460
§ 371 (c)(1),
(2), (4) Date: Feb. 8, 2013

(87) PCT Pub. No.: WO2012/020467
PCT Pub. Date: Feb. 16, 2012

(65) Prior Publication Data
US 2013/0136226 A1    May 30, 2013

(51) Int. Cl.
*H05G 1/02*    (2006.01)
*G01N 23/04*   (2006.01)
*A61B 6/02*    (2006.01)
*A61B 6/14*    (2006.01)
(Continued)

(52) U.S. Cl.
CPC .............. *G01N 23/046* (2013.01); *A61B 6/027* (2013.01); *A61B 6/14* (2013.01); *A61B 6/4452* (2013.01); *A61B 6/035* (2013.01)
USPC ........................................................ 378/197

(58) Field of Classification Search
CPC .......... A61B 6/14; A61B 6/501; A61B 6/035; A61B 6/4452; A61B 6/025; A61B 6/027
USPC ............................ 378/4, 21, 38–40, 193–197
See application file for complete search history.

(56) References Cited

U.S. PATENT DOCUMENTS 5,921,927 A    7/1999   McArdle
6,169,780 B1   1/2001   Yoshimura et al.

FOREIGN PATENT DOCUMENTS

JP    H 02-093452 A    4/1990
JP    H 10-225455 A    8/1998
(Continued)

OTHER PUBLICATIONS

European Search Report for corresponding EP Application No. 10855868 dated Feb. 11, 2014 (6 pages).
(Continued)

*Primary Examiner* — Courtney Thomas
(74) *Attorney, Agent, or Firm* — Merchant & Gould P.C.

(57) ABSTRACT

An X-ray photographing device includes an X-ray irradiating unit (10) for irradiating an object (5) with an X-ray beam (6) having a slit shape from a source (11*a*), and an imaging member (7) provided with a surface (7*a*) to receive the X-ray beam. A pivot drive unit causes the irradiating unit (10) and the imaging member (7) to pivot about a pivoting center line (La) around the object (5), and a sub-drive unit (30) causes the imaging member (7) to have a local motion in a circumferential direction with a shift width (Mw). A width (W2) of the surface (7*a*) in the circumferential direction is smaller than the shift width (Mw) and the local motion is a local rotation motion made on the rotation center line (Lc). This configuration reduces the cost of the device, reduces vibrations of the imaging member (7), and enhances operating efficiency.

7 Claims, 9 Drawing Sheets

(51) Int. Cl.
*A61B 6/00* (2006.01)
*A61B 6/03* (2006.01)

(56) References Cited

FOREIGN PATENT DOCUMENTS

| JP | 2003-175031 A | 6/2003 |
| JP | 2005-177047 A | 7/2005 |
| JP | 2006-212229 A | 8/2006 |
| WO | WO 00/00087 | 1/2000 |

OTHER PUBLICATIONS

International Search Report for PCT/JP2010/063460 mailed Sep. 21, 2010 (2 pgs.)

US 8,979,366 B2

X-RAY PHOTOGRAPHING DEVICE

This application is a National Stage Application of PCT/JP2010/063460, filed 9 Aug. 2010, which application is incorporated herein by reference. To the extent appropriate, a claim of priority is made to the above disclosed application.

TECHNICAL FIELD

The present invention relates to an X-ray photographing device for generating an X-ray image of an object on the basis of image data obtained with an X-ray imaging member receiving an X-ray beam radiated by an X-ray unit and transmitted through the object. The X-ray photographing device is used in, for example, a dental practice.

BACKGROUND ART

For example, an X-ray photographing device for dental practices is disclosed which includes an X-ray irradiating unit for irradiating an object with an X-ray beam, an X-ray imaging unit provided with a light-receiving surface for receiving an X-ray beam transmitted through the object, and a drive unit for causing the X-ray imaging unit to perform pivoting motion around the object for a CT scan and a panoramic exposure (for example, Patent Documents 1 and 2).

PRIOR ART DOCUMENTS

Patent Documents

[Patent Document 1]
JP10-225455
[Patent Document 2]
JP2003-175031 (FIG. 14)

SUMMARY OF INVENTION

Problems to be Solved by the Invention

To perform the CT scan and the panoramic exposure by the X-ray photographing device, when an X-ray imaging member for CT scan is used, the X-ray photographing device having such an X-ray imaging member will be expensive because the X-ray imaging member for the CT photographing, having a wide light-receiving surface, is expensive.

In addition, in the X-ray photographing device, it is assumed that the X-ray imaging member is moved to cause to perform a local motion which is different from the pivoting motion on a pivoting center line, and that the local motion involves temporal stop and restart of the X-ray imaging member such as a reciprocating motion in a line or an arc. This may be a cause for vibrating the X-ray imaging member because an inertia force caused by acceleration and deceleration may act on the X-ray imaging member due to necessity of accelerating and decelerating the X-ray imaging member. In addition, because just after the start and stop of the X-ray imaging member, a moving speed of the X-ray imaging member may decrease, an operation efficiency of X-ray photographing may decrease due to the temporal stop and the restart.

The present invention, having been developed in consideration of such a circumference, in an X-ray photographing device provided with an X-ray irradiating unit and an X-ray imaging member, aims to reduce a cost of the X-ray photographing device, further aims to reduce the vibrations of the driven member caused by the local motion when a driven member, being at least one of the X-ray irradiating unit and the X-ray imaging member, is caused to perform a local motion which is different from a pivoting motion, and aims to enhance an operating efficiency.

Measures for Resolving the Problems

An X-ray photographing device comprising: an X-ray irradiating unit (10) configured to irradiate an object (5) with an X-ray beam (6); an X-ray imaging member (7) having the light-receiving surface (7a) configured to receive the X-ray beam (6) transmitted through the object (5); a pivot drive unit (20) configured to cause the X-ray irradiating unit (10) and the X-ray imaging member (7) to have a pivoting motion on a pivoting center line (La) around the object (5) and the control unit 60 configured to control the pivot drive unit (20), further comprising a sub-drive unit (30, $30_1$ to $30_5$, 22), controlled by the control unit (60), configured to cause a driven member (7, 10) which is at least one of the X-ray irradiating unit (10) and the X-ray imaging member (7) to have a local motion which is different from the pivoting motion with a shift width (Mw) in a predetermined direction, wherein a width (W2) of the light-receiving surface (7a) in the predetermined direction is smaller than the shift width (Mw), and the local motion is a motion made on the rotation center line (Lc).

According to this, because the width of the light-receiving surface in the predetermined direction is smaller than the shift width, in the predetermined direction, of the driven member for performing the local rotation motion driven by the sub-drive unit, the X-ray imaging member which is less expensive than X-ray imaging member having a light-receiving surface having a size corresponding to the moving width, so that a cost for the X-ray photographing device can be reduced.

In addition, because the driven member which is at least one of the X-ray irradiating unit and the X-ray imaging member performs the local rotation motion, operations of a temporary stop made when the driven member performs an arc motion or a linear motion and a restart after the temporary stop can be eliminated. As the result, because acceleration and deceleration acting on the driven member can be reduced, an inertial force based on the acceleration and deceleration can be reduced, which reduces vibrations of the driven member caused by the inertial force, so that a durability of the driven member can be enhanced. In addition, a decrease in speed due to the temporary stop and restart of the driven member from start to finish of the X-ray photographing can be suppressed, so that an operation efficiency of the X-ray photographing can be enhanced because of speed-up of the driven member.

In some embodiments, the rotation center line (Lc) is arranged such that the object (5) is always positioned between the X-ray irradiating unit (10) and the X-ray imaging member (7) when one revolution of the driven member (7, 10) is made on the rotation center line (Lc).

With this configuration, at a given timing or during a given continuous period while the driven member makes one revolution on the center at the rotation center line, the X-ray photographing become possible through the X-ray imaging member, so that an efficiency of the photographing can be enhanced.

In further embodiments the pivot drive unit (20) causes the X-ray irradiating unit (10) and the X-ray imaging member (7) to have shift pivoting motions, each having a shift pivoting quantity (S) smaller than one revolution of the pivoting motion to locate the X-ray irradiating unit (10) and the X-ray imaging member (7) at a shift pivot position (Ps), the sub-drive unit (30, $30_1$ to $30_5$, 22) causes a driven member (7, 10) to perform the local rotation motion at each of the shift pivot positions (Ps), and the shift pivot positions adjoining to each other in the circumferential direction are such positions that an overlap range (Mo) where the circumferential direction shift ranges (Mc) of the local rotation motion are overlapped each other is formed.

According to this, using the X-ray imaging member having the width of the light-receiving surface in the predetermined direction smaller than the shift width of the driven member in the predetermined direction enable to perform a CT scan and panoramic exposure, a panoramic exposure and an a cephalometric roentgenography.

According to still further embodiments, the rotation center line (Lc) is substantially in parallel to a line (Lp) in parallel to an orthogonal line of the pivoting center line (La), and the predetermined direction is a direction in parallel to the pivoting center line (La).

According to this, by using the X-ray imaging member having the width in the pivoting center line direction smaller than the shift width of the driven member in the pivoting center line, X-ray photographing is made possible with a large photographing area in the pivoting center line though a low cost X-ray imaging member is used.

In further embodiments the sub-drive unit ($30, 30_1$ to $30_3$) includes an interval adjusting mechanism (49) capable of changing an interval (d1, d3) between the rotation center line (Lc) and the driven member (7, 10). According this, changing the interval between the rotation center line and the driven member, which increases a degree of freedom in setting the shift width, further makes it possible to change the imaging area on the light-receiving surface without change in the shift pivot quantity, so that a convenience of the X-ray photographing device can be enhanced.

In further embodiments, the interval adjusting mechanism (49) changes the interval (d1, d3) in accordance with a position of the driven member (7, 10) on the motion route (M) of a local rotation motion.

According to this, during the local rotation motion or the pivoting motion of the driven member, because the interval between the object and the driven member can be changed in accordance with the position of the driven member on the motion route, the motion route can be set in accordance with the shape of the object, so that the convenience of the photographing can be enhanced. In addition, the local rotation motion of the driven member is made, for example, circularly flatted in the irradiation direction. This reduces a variation width in enlargement and reduction ratio for correcting the image data obtained by the X-ray imaging member, which makes it possible to enhance accuracy in photographing.

According to still further embodiments the driven member (7, 10) is the X-ray imaging member (7), and the X-ray irradiating unit (10) includes a collimator (12c) defining an irradiation range and an irradiation direction of the X-ray beam (6) applied to the object (5), and the collimator (12c) moves to track the X-ray imaging member (7) to keep a status in which the collimator (12c), the object (5), and the light-receiving surface 7a are positioned on a line.

With this configuration, because the collimator moves to track the X-ray imaging member while the status is kept such that the collimator, the object, the light-receiving surface of the X-ray imaging member are positioned in a line, the X-ray beam having the irradiation range and the irradiation direction defined by the collimator can be oriented accurately to the object and the light-receiving surface, so that the accuracy in photographing can be enhanced.

Advantageous Effect

According to the present invention, in the X-ray photographing device including the X-ray irradiating unit and the X-ray imaging member, with reduction in cost of the X-ray photographing device, when the driven member, being at least one of the X-ray irradiating unit and X-ray imaging member, is caused to perform the local motion which is different from the pivoting motion, vibrations of the driven member caused by the local motion can be reduced and thus, operating efficiency can be enhanced.

BRIEF DESCRIPTION OF DRAWINGS

FIGS. 2A and 2B are schematic drawings of a main part around an X-ray imaging member of the X-ray photographing device, wherein FIG. 2A is a side view including a cross section view, and FIG. 2B is a bottom plan view of the main part in FIG. 2A.

FIG. 3A and FIG. 3B are schematic drawings illustrating a local rotation motion of the X-ray imaging member when an arm of the X-ray photographing device in FIG. 1 is positioned at one pivoting position, wherein FIG. 3A is an upper plan view and FIG. 3B is a front view.

FIG. 11C is an enlarged view, viewed from c in FIG. 11B.

FIG. 12C is an enlarged view, viewed from c in FIG. 12B.

MODE FOR CARRYING OUT THE INVENTION

Hereinbelow embodiments of the present invention will be described with reference to FIGS. 1 to 12.

FIGS. 1 to 4 are drawings for illustrating the first embodiment of the present invention.

Figure 1:
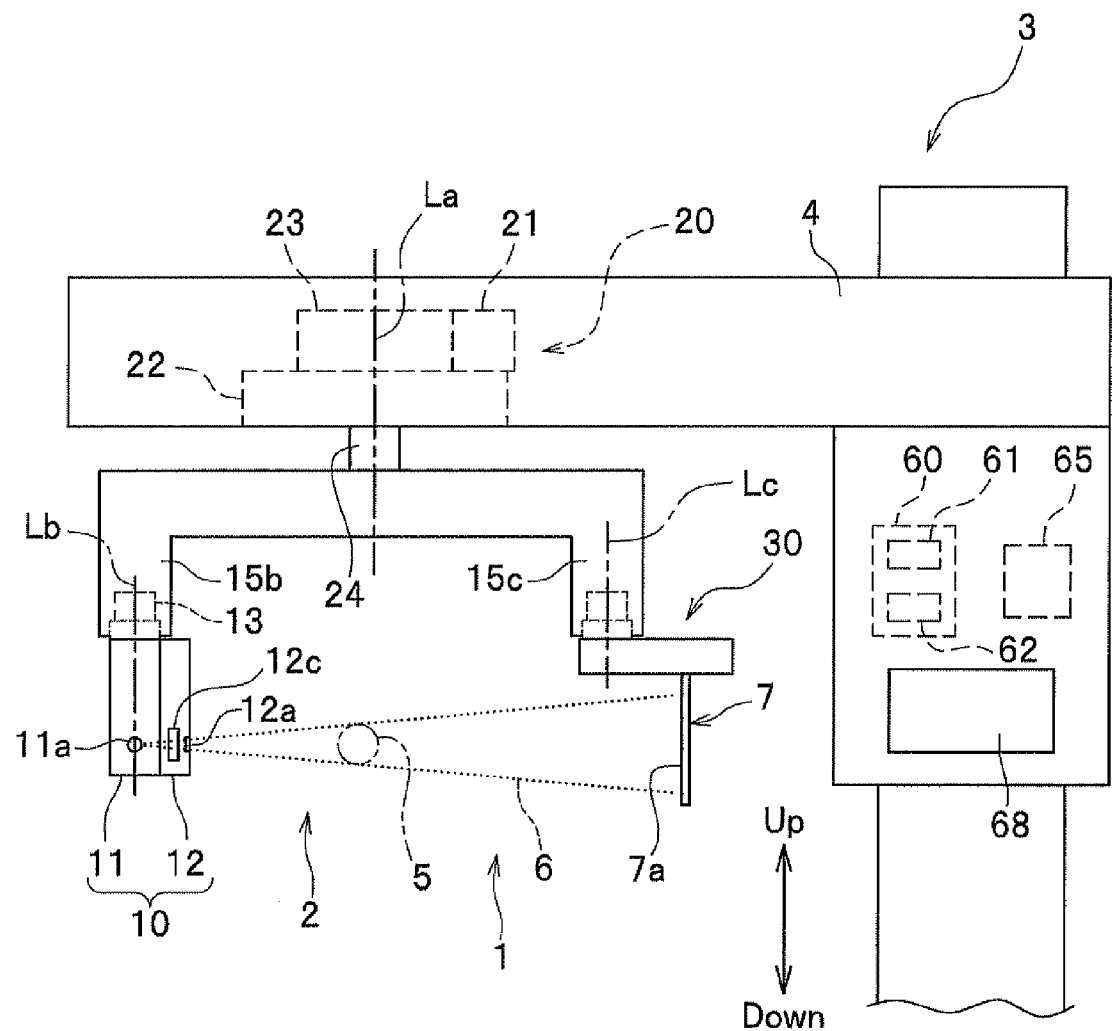
FIG. 1 shows a first embodiment of the present invention and is a front view, as a main-part schematic drawing, of an X-ray photographing device.

Referring to FIG. 1, an X-ray photographing device 1 of the first embodiment is used for the human being in dental practices as medical care.

The X-ray photographing device 1 includes a main unit 2, and a supporting unit 3 having a frame 4 for supporting the main unit 2. The supporting unit 3 is installed on a construction (not shown) on which the X-ray photographing device 1 is installed, and the frame 4 supports the main unit 2 at a position adjustable in an up-down direction with the supporting unit 3. As another example, the main unit 2 may have a mechanism for adjusting the position thereof in the up-down direction relative to the frame 4.

A main unit 2 includes an X-ray irradiating unit 10 for irradiating an object 5 (for example, a dental arch, the head including the dental arch) with an X-ray beam 6, an arm 15 as a supporting member for supporting the X-ray irradiating unit 10 and the X-ray imaging member 7 which are disposed at opposite positions across the object 5 in an radiation direction of the X-ray beam 6 generated by the X-ray irradiating unit 10, a pivot drive unit 20 for pivoting the arm 15 for causing the X-ray irradiating unit 10 and the X-ray imaging member 7 to perform pivoting motions on a pivoting center line La around the object 5, an imaging side drive unit 30 for causing the X-ray imaging member 7 as a driven member to perform a local rotation motion which is different from the pivoting motion, a control unit 60 for controlling the pivot drive unit 20, the imaging side drive unit 30, and X-ray photographing of the object 5, an image processing unit 65 for processing image data obtained by the X-ray imaging member 7, an operating unit 68 to be operated by an operator, and a display device (not shown) for displaying an image detected by the X-ray imaging member 7.

Regarding this, the pivot drive unit 20, a sub-drive unit which is the imaging side drive unit 30 in the first embodiment, and a drive unit 13 described later form a drive unit of the X-ray photographing device 1.

The X-ray irradiating unit 10 supported by an irradiation side supporting member 15b of the arm 15 includes a X-ray irradiating member 11 having an X-ray source 11a for irradiating an X ray and a slit member 12 as an X-ray beam forming member for forming the X-ray beam from the X-ray source 11a into the X-ray beam 6 to have a slit shape in cross section. The slit member 12 includes an irradiation unit configured with a collimator 12c for defining an irradiation range and the radiation direction of the X-ray beam 6, and with a slit 12a for allowing the X-ray beam formed by the collimator 12c through the slit 12a. Accordingly, the collimator 12c and the slit 12a for irradiation of the X-ray beam 6 and a light-receiving surface 7a are disposed at opposite positions across the object 5 in the radiation direction of the X-ray beam 6 regarding the arm 15 (see FIG. 3).

The X-ray irradiating member 11 and the slit member 12 are attached to the arm 15 and driven by the drive unit 13 controlled by the control unit 60 to have a rotation motion or a linear motion so as to be movable relative to the arm 15.

More specifically, the drive unit 13 moves the X-ray source 11a, the collimator 12c, and the slit 12a to trace the light-receiving surface 7a having the local rotation motion with a state in which the X-ray source 11a, the collimator 12c, the slit 12a, the object 5, and the light-receiving surface 7a are located on a line. In the first embodiment, the drive unit 13 causes the X-ray source 11a, the collimator 12c, and the slit 12a to have a rotation motion on a radiation center line Lb passing through the X-ray source 11a and in parallel to a pivoting center line La so that the X-ray source 11a, the collimator 12c, and the slit 12a move in an arc or a circumferential direction. As another example, the drive unit 13 may cause the X-ray source 11a, the collimator 12c, and the slit 12a to have a linear motion.

The X-ray imaging member 7 having the light-receiving surface 7a is a two-dimensional X-ray imaging unit configured with an image sensor such as a CMOS sensor, a CdTe sensor, and a CCD sensor. In the embodiment described below, the CMOS sensor is used as the image sensor.

As shown in FIG. 2, the light-receiving surface 7a has a long and thin stripe shape having a width W1 in a longitudinal direction thereof being longer than a width W2 in a direction orthogonal with the longitudinal direction. The longitudinal direction of the light-receiving surface 7a is substantially in parallel to the pivoting center line La in the first embodiment in a state where the X-ray imaging member 7 is supported by the arm 15.

In the specification and claims of this application, expression of "substantially" includes a case where there is no modifier of "substantially" and means a range in which there is no effective difference in operation and advantageous effect in comparison with the case where there is no modifier of "substantially".

Referring to FIG. 1, the pivot drive unit 20, installed at the frame 4, includes a servo motor 21 as a pivoting actuator for rotating the arm 15, an XY table 22 driven by the servo motor 21 as a two-dimensional drive unit for moving the arm 15 on a horizontal plane as a two-dimensional plane orthogonal with the pivoting center line La, a transmitting mechanism 23 having a reduction mechanism for transmitting the drive force from the servo motor 21 to the XY table 22, and a connecting shaft 24, as a connecting member, for connecting the servo motor 21 to the arm 15 through the transmission mechanism 23 and the XY table 22. The arm 15 rotates on the pivoting center line La as a result of rotary drive by the servo motor 21 through the transmitting mechanism 23, the XY table 22, and the connecting shaft 24. This rotates the X-ray irradiating member 10 and the X-ray imaging member 7.

"Pivoting" includes a case where pivoting one or more turn on the pivoting center line La and a case where pivoting less than one turn. In addition, the reduction mechanism of the transmitting mechanism 23 and reduction mechanisms of transmitting mechanisms 33 and 51 described later, and a reduction mechanism 48 (see FIG. 2) is configured with, for example, a warm gear mechanism.

Figure 2A:
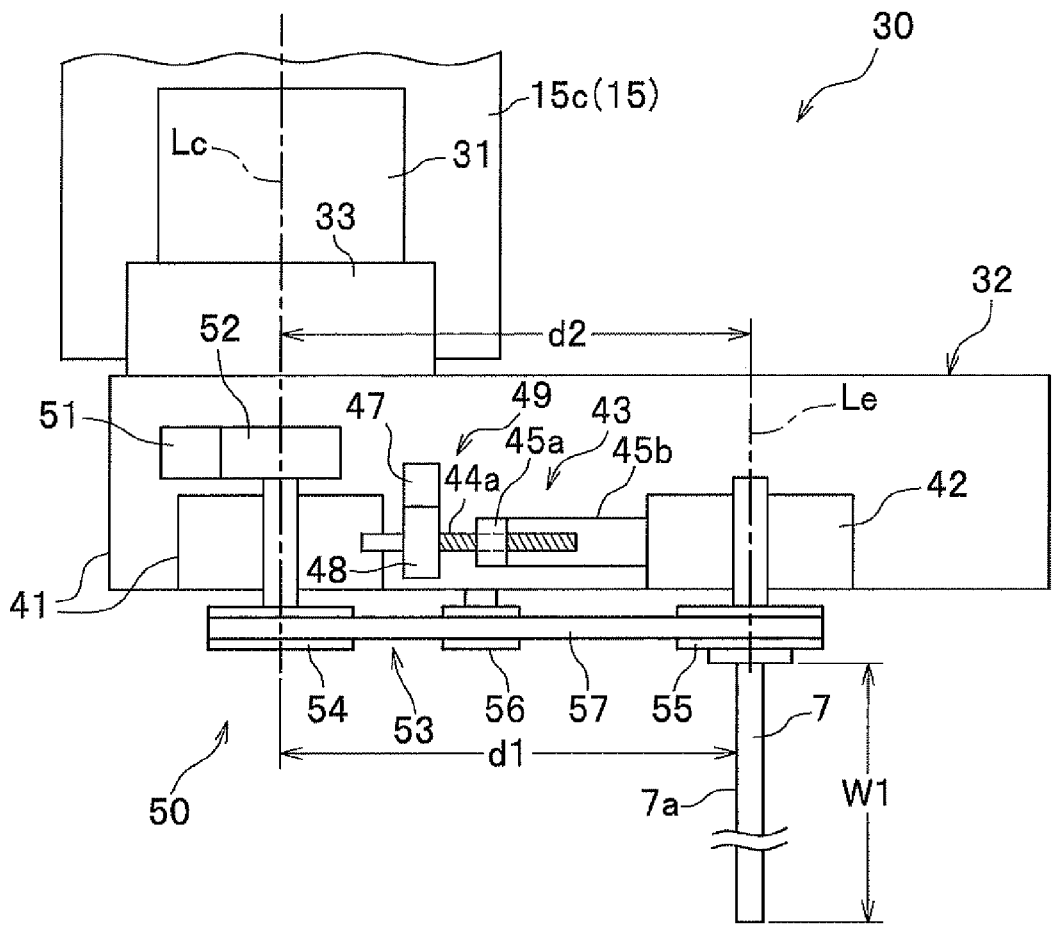
Figure 2B:
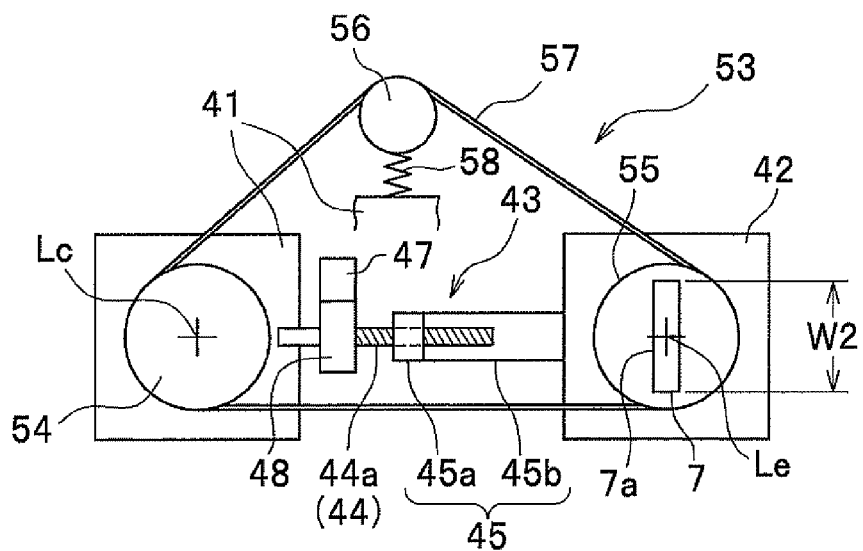

Referring to FIGS. 1 and 2A and 2B, the imaging side drive unit 30 installed at the arm 15 includes a servo motor 31 as the imaging side actuator, a holding member 32 for holding the X-ray imaging member 7, and the transmitting mechanism 33, including a reduction mechanism, for transmitting a driving force of the servo motor 31 to the holding member 32. In addition, the X-ray imaging member 7 and the light-receiving surface 7a are rotary driven by the servo motor 31 through the transmitting mechanism 33 and the holding member 32 to have a local rotation motion (see FIG. 3) on a rotation center line Lc which is line other than the pivoting center line La.

Further referring FIG. 3, the local rotation motion is defined on the basis of an interval d1 between the rotation center line Lc and the X-ray imaging member 7 in a radial direction from a center on the rotation center line Lc and an interval d2 described later, and if it is assumed that a circumferential direction on the pivoting center line La (see FIG. 1) as a center is defined as a predetermined direction, the local rotation motion is a motion within a range of a shift width Mw in the predetermined direction. In addition, a width W1 which is a width of the light-receiving surface 7a in the predetermined direction is smaller than a shift width Mw. In addition, in the local rotation motion, the light-receiving surface 7a rotates in such a status that the longitudinal direction of the light-receiving surface 7a is substantially in parallel to the pivoting center line La, i.e., in a pivoting center line direction which is in parallel to the pivoting center line La (which is also the up-down direction in the first embodiment).

Further, in a case where one rotation of the X-ray imaging member 7 is made relative to the arm 15 on the rotation center line Lc, the rotation center line Lc is always positioned between the slit 12a of the X-ray irradiating unit 10 and the light-receiving surface 7a of the X-ray imaging member in the radiation direction of the X-ray beam 6.

Referring to FIG. 2, the holding member 32 is rotatably supported by an imaging side supporting member 15c of the arm 15 on the rotation center line Lc and rotates on the rotation center line Lc. Further, the X-ray imaging member 7 is rotatably supported by the holding member 32 on an autorotation center line Le which is a slave-rotation center line and positioned with a predetermined interval d2 from the rotation center line Lc.

More specifically, the base holding member 32 includes a first base 41 rotationally driven by the servo motor 31 through the transmitting mechanisms 33, a second base 42 for rotatably supporting the X-ray imaging member 7 on the autorotation center line Le and being movably supported by the first base 41 in a radial direction of the rotation center line Lc, a connecting member 43 for connecting the first base 41 and the second base 42 and extendable and shrinkable in a radial direction of the rotation center line Lc, a servo motor 47 as an actuator for adjusting an interval for causing extension and shrinking of the connecting member 43 in the radial direction of the rotation center line Lc, and a rotating mechanism 50 for rotationally driving the X-ray imaging member 7 and the light-receiving surface 7a on the autorotation center line Le. The connecting member 43 defines the predetermined interval d2 between the rotation center line Lc and the autorotation center line Le.

The rotating mechanism 50 is rotatably supported by the first base 41 and includes the servo motor 51 as a rotation actuator, a transmitting mechanism 52 having a reduction mechanism, and a transmitting mechanism 53 for rotating the X-ray imaging member 7 by rotation drive by the servo motor 51 through the transmitting mechanism 52.

The transmitting mechanism 53 includes a drive pulley 54 as a drive part, a driven pulley 55 rotationally supported by the second base 42 as a driven part to which the X-ray imaging member 7 is fixed, an idle pulley 56 rotatably supported by the first base 41, and a belt 57 as an endless transmitting belt wrapped around the drive pulley 54, and the pulleys 55, 56. The idle pulley 56 is spring-loaded with a spring 58 as a loading member and functions as a tensioner for providing an extension force on the belt 57.

A rotation center line of the drive pulley 54 is coaxial with the rotation center line Lc, but may be in parallel to the rotation center line Lc as another example. In addition, a rotation center line of the driven pulley 55 is on the autorotation center line Le.

The connecting member 43 includes a first connecting member 44 installed on the first base 41, a second connecting member 45, installed on a second base 42, being linearly movable in a radial direction of the rotation center line Lc relatively to the first connecting member 44. In the embodiment, the first connecting member 44 is configured with a threaded rod 44a, rotatably supported by the first base 41, rotationally driven by the servo motor 47. In addition, the second connecting member 45 is configured with a thread part 45a screwed on the threaded rod 44a and a connecting rod 45b which rotatably supports the thread part 45a as the connecting member with the threaded rod 44a and is fixed to the second base 42 to be movable in the radial direction together with the connecting rod 45b and the second base 42.

The servo motor 47 rotationally drives the threaded rod 44a through the reduction mechanism 48 functioning as a transmission mechanism to rotate the thread part 45a to move the second connecting member 45 along the first connecting member 44 in the radial direction of the rotation center line Lc to adjust the interval d1 and the interval d2.

Accordingly, the connecting member 43, the servo motor 47 and the reduction mechanism 48 form an interval adjusting mechanism 49 able to change the interval d1 between the rotation center line Lc and the light-receiving surface 7a of the X-ray imaging member 7 and the predetermined interval d2.

Figure 3A:
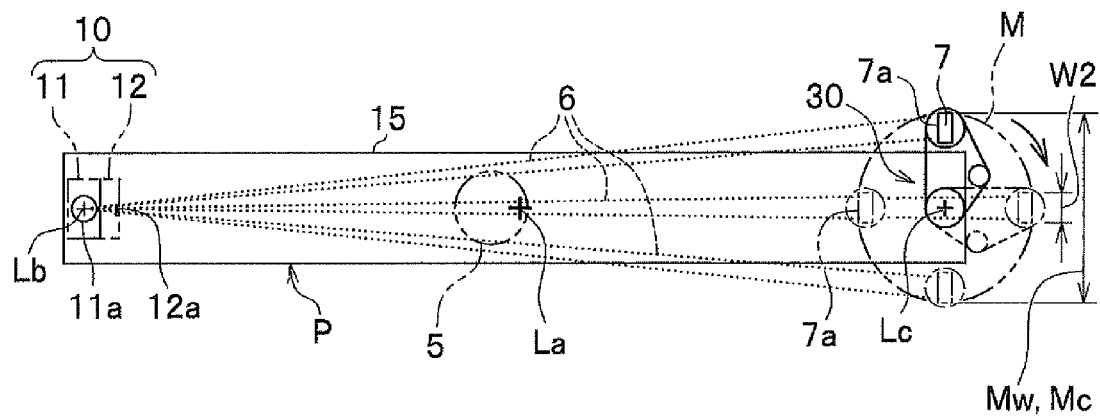
Figure 3B:
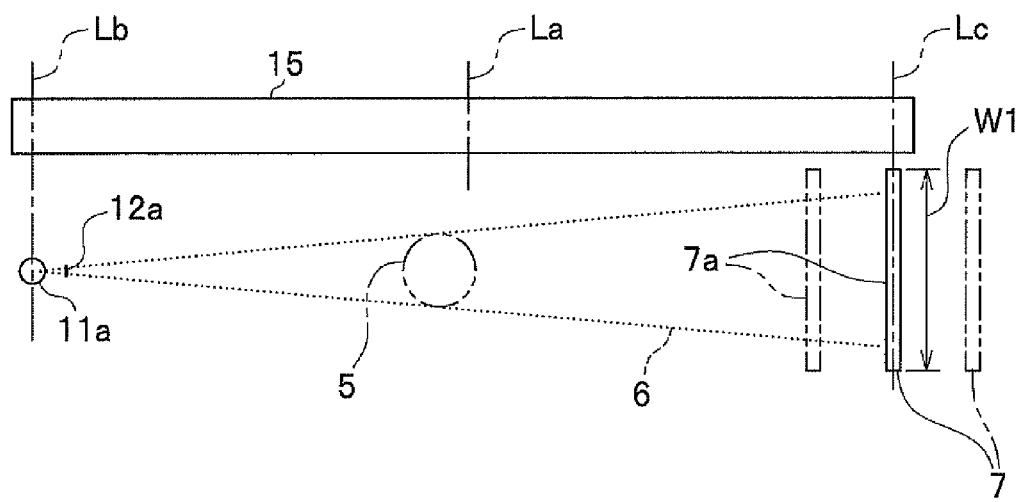
Figure 4:
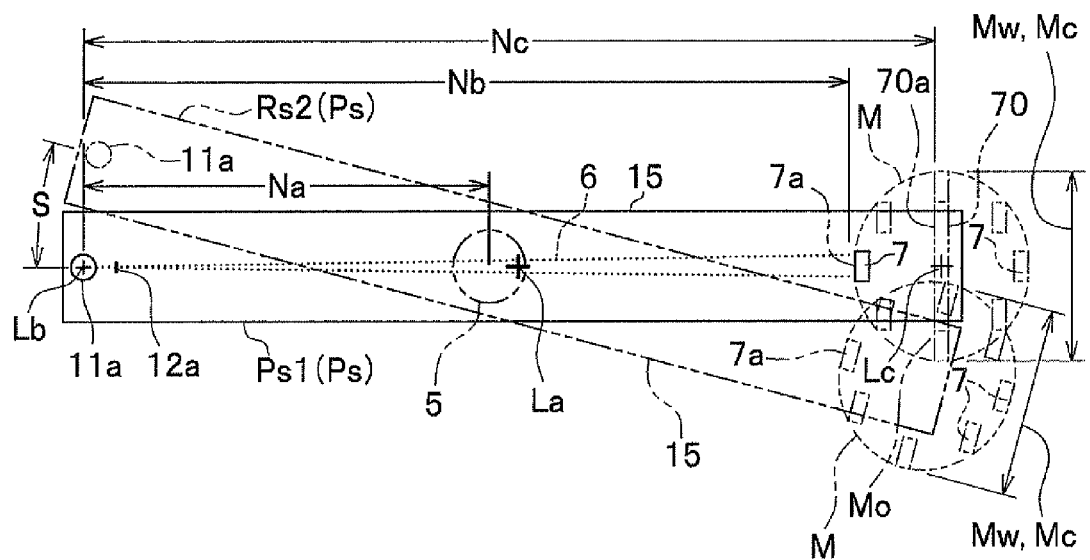
FIG. 4 is an upper plan view of a main part schematic drawing for illustrating the pivoting motion and a local rotation movement when the CT scan is made by the X-ray photographing device of FIG. 1.

Accordingly, the servo motor 47 is operated to change a length of the connecting member 43 to change the interval d1 and the certain interval d2 to change the shift width Mw (see FIGS. 3A and 3B), so that an imaging area on the light-receiving surface 7a having a local rotation motion without changing the pivoting position P of the arm 15 can be changed (see FIG. 4). For example, the shift width Mw and the imaging area of the light-receiving surface 7a become larger than the shift width Mw and the imaging area in the case shown in FIG. 3A by making the connecting member 43 longer than that in the status shown in FIGS. 2A and 2B.

In the first embodiment, the length of the connecting member 43 is constant at a given position of the X-ray imaging member 7 having a local rotation motion and at a given pivoting position P of the arm 15 having a pivoting motion.

Referring also to FIGS. 3A and 3B, the servo motor 51 orients the light-receiving surface 7a to the slit 12a across the object 5 in a radial direction to cause the light-receiving surface 7a to always receive the X-ray beam 6 transmitted through the object 5. For this purpose, the servo motor 51, controlled by the control unit 60, rotationally drives the drive pulley 54 and the driven pulley 55 in synchronization with the local rotation motion of the X-ray imaging member 7. Rotation speeds of the drive pulley 54 and the driven pulley 55 are equally set in the embodiment, but may be set to different rotation speeds.

The light-receiving surface 7a driven by the servo motor 51 rotates on the axis thereof so as to be in parallel to a plane orthogonal with a line passing through the pivoting center line La and the rotation center line Lc at any position on a motion route M (an outline outer circumference of motion route M is shown in FIGS. 3A and 3B). As another example, rotation on its own axis may be made to cause the light-receiving surface 7a to orient to the radiation center line Lb. As a still another example, the rotating mechanism 50 may include an interlocking mechanism for transmitting rotation of the servo motor 31 to the drive pulley 54 (for example, configured with a gear mechanism) in place of the servo motor 51, so that the servo motor 31 can rotationally drive the drive pulley 54 in synchronization with the local rotation motion of the X-ray imaging member 7 through the interlocking mechanism.

Accordingly, as shown in FIGS. 3A and 3B, in a status where the arm 15 driven by the pivot drive unit 20 (see FIG. 1), i.e., the X-ray irradiating unit 10 and the X-ray imaging member 7, is located at the pivoting position P, the X-ray imaging member 7 rotates on the rotation center line Lc (in FIGS. 3A and 3B, positions are shown with an angular interval of substantially 90 degrees). In addition, the X-ray irradiating unit 10 is rotationally driven by the drive unit 13 (see FIG. 1) in a circumferential direction regarding the pivoting center line La to move the slit 12a and the light-receiving surface 7a to opposite positions in an irradiation direction of the X-ray beam 6 across the object 5 in accordance with the rotation position of the light-receiving surface 7a.

The control unit 60 includes: a detecting unit 61 including position detecting means (which, for example, may be configured with an encoder) for detecting the pivoting position P (which also the pivoting position P of the arm 15) of the slit 12a and the light-receiving surface 7a and a rotation position of the X-ray imaging member 7 on the rotation center line Lc (that is, a position on the motion route M); and a control unit 62 including a central processing unit. The control unit 62 control operation of each of the servo motor 21, the servo motor 31, the servo motor 47, and the servo motor 51 in accordance with detection signals from the detecting unit 61 and signals set by the operating unit 68.

The image processing unit 65 processes image data obtained in the X-ray photographing on the X-ray imaging member 7 to generate CT images, panorama images, cephalo images.

In addition, a setting is made through the operating unit 68 for switching of the respective photographing modes through the operating unit 68 such as a CT scan, panorama imaging, cephalo imaging for the object 5, a setting of the certain interval d2, an initial pivot position P of the arm 15 and a shift pivoting quantity S at startup of photographing.

Referring to FIGS. 1 and 4, operation of the X-ray photographing device 1 will be described with an example in which CT scanning is made with the X-ray photographing device 1.

When the CT scan is selected with the operating unit 68, the slit 12a and the light-receiving surface 7a are positioned at a first shift pivot position Ps1 as an initial pivoting position in the circumferential direction of the pivoting center line La. At the first shift pivot position Ps1, the X-ray imaging member 7 is driven by the servo motor 31 to rotate from a first position set as an initial portion on the motion route M of a local rotation motion in the rotation direction (clockwise direction in FIG. 4) to make a continuous one turn around the rotation center line Lc through movement on the motion route M. During this, under control by the control unit 60, the X-ray beam 6 is detected by the X-ray imaging member 7 through the light-receiving surface 7a at every position with a predetermined interval (for example a predetermined angle of the local rotation motion) to perform the X-ray photographing, so that a shift image data group formed with a lot of image data pieces at positions on the motion route M.

While the X-ray imaging member 7 pivots on the pivoting center line La by one turn or over one turn from the first shift pivot position Ps1, the image processing unit 65 at the respective pivot positions Ps, an image correcting process for correcting the image data obtained at the respective position on the motion route M is performed to obtain an image corresponding to a virtual X-ray imaging member 70 described later.

As shown in FIG. 4, if it is assumed that the virtual X-ray imaging member 70 has a light-receiving surface 70a (hereinafter referred to as "virtual light-receiving surface 70a") having a planar shape having, for example, a circumferential direction width (width in the described predetermined direction) which is equal to the shift width Mw, the image processing unit 65 performs the image correcting process on the image data obtained by the X-ray imaging member 7 on the basis of the enlargement/reduction ratio N calculated by the following equation.

$$N = (Nc/Na)/(Nb/Na)$$
$$= Nc/Nb$$

Where
Na: a distance between the X-ray source 11a and a photographing part of the object 5;
Nb: a distance between the X-ray source 11a and the light-receiving surface 7a; and
Nc: a distance between the X-ray source 11a and the virtual light-receiving surface 70a.

In addition, when the virtual X-ray imaging member 7 has the light-receiving surface 7a in an arc with a center on the radiation center line Lb, the CT image can be also obtained by a similar image correcting process using the enlargement/reduction ratio N.

When the X-ray imaging member 7 makes one revolution on a center at the rotation center line Lc, the servo motor 21 causes the arm 15 to perform pivoting motions, each pivoting motion having a shift pivoting quantity S smaller than one revolution motion in the pivoting direction (clockwise in FIG. 4) so that the slit 12a and the light-receiving surface 7a are positioned at a second shift pivoting position Ps2. The shift pivoting motion of the arm 15 shifts the slit 12a and the light-receiving surface 7a from the first shift pivot position Ps1 to the second shift pivoting position Ps2.

In this operation, at a transition during which the slit 12a and the light-receiving surface 7a shift from the first shift pivot position Ps1 to the second shift pivoting position Ps2, the X-ray imaging member 7 continues the local rotation motion without a temporary stop and a restart from the temporary stop, but the X-ray photographing is not made. In addition, as another example, the respective drive units 20, 30 may finish photographing within a pivoting range of less than one pivoting of the X-ray imaging member 7 at the first shift pivot position Ps1, and may cause the arm 15 to have a shift pivoting motion to the next shift pivot position Ps within the remaining pivoting range up to one pivoting. In addition, the X-ray imaging member 7 continues the local rotation motion until the CT scan will have been finished.

Referring to FIG. 4, the shift pivoting quantity S is set to form an overlap range Mo where the circumferential direction shift ranges Mc of the local rotation motion (equivalent to the shift width Mw, in the embodiment) at the respective adjoining shift pivot positions Ps adjoining in the circumferential direction are overlapped with each other. The control unit 60 obtains other shift image data groups with the X-ray imaging member 7 at a plurality of different positions on the motion route M of the X-ray imaging member 7 resulting from the local rotation motion in the circumferential direction shift range Mc of the local motion at the respective shift pivot positions Ps.

Here, the shift pivoting quantity S is set to have values equal to each other in the embodiment. However, as another example, these values may be set to different values.

The slit 12a and the light-receiving surface 7a shift from the first shift pivot position Ps1 to the second shift pivoting position Ps2, and the slit 12a and the light-receiving surface 7a further have successive pivoting motions in the pivoting direction, each pivoting motion having the shift pivoting quantity S until one revolution on the pivoting center line La is made, so that the CT photographing is finished.

The image processing unit 65 generates a whole image by collecting the shift image data groups at the respective shift pivot positions Ps1.

In addition also in a case where a panoramic exposure, or a cephalometric roentgenography is made by the X-ray photographing device 1, photographing is made with the X-ray imaging member 7 having a local rotation motion similar to the CT scan at one or more shift pivot positions Ps using the XY table 22 as required.

Next, will be descried an operation and advantageous effects of the first embodiment having the above-described configuration.

The X-ray photographing device 1 includes the imaging side drive unit 30 for causing the X-ray imaging member 7 to have the local motion which is different from the pivoting motion of the arm 15 at the shift width Mw of the light-receiving surface 7a if it is assumed that the circumferential direction on the pivoting center line La is defined as a predetermined direction. The width W1 of the light-receiving surface 7a in the predetermined direction is smaller than the shift width. The local motion is a local rotation motion on the rotation center line Lc.

With the configuration, a cost for the X-ray photographing device 1 can be reduced because of the use of the X-ray imaging member 7 which is less expensive than an X-ray imaging member having a light-receiving surface having a size corresponding to the shift width Mw because the width W1 of the light-receiving surface 7a in the predetermined direction is smaller than the shift width Mw of the local rotation motion of the light-receiving surface 7a driven by the imaging side drive unit 30.

In addition, because the X-ray imaging member 7 can perform the rotational motion, operations of a temporary stop or a restart after the temporary stop made when the X-ray imaging member 7 performs an arc motion or a linear motion can be eliminated. As the result, acceleration and deceleration acting on the X-ray imaging member 7 can be reduced, so that an inertial force based on the acceleration and deceleration can be decreased. This reduces vibrations of the driven member, which are caused by the inertial force, enhancing a durability of the X-ray imaging member 7 having a slender shape. In addition, because decrease in speed due to the temporary stop and the restart of the X-ray imaging member 7 from a start to an end of X-ray photographing can be suppressed, enhancement in an efficiency of X-ray photographing operation by a high speed motion of the X-ray imaging member 7 can be provided.

The rotation center line Lc is arranged such that the object 5 is positioned always between the X-ray irradiating unit 10 and the X-ray imaging member 7 in a case where the X-ray imaging member 7 makes one revolution on a center at the rotation center line Lc. This allows the X-ray photographing through the X-ray imaging member 7 at a given timing or during a given continuous period during one revolution of the X-ray imaging member 7 on the rotation center line Lc, so that the efficiency in photographing operation can be enhanced.

The pivot drive unit 20 causes the X-ray irradiating unit 10 and the X-ray imaging member 7 to have the shift pivoting motions, each of the shift pivoting motions having the shift pivoting quantity S which is smaller than the pivoting motion of one revolution so that the X-ray irradiating unit 10 and the X-ray imaging member 7 are located at shift pivot positions P, Ps12S. The imaging side drive unit 30 causes the X-ray imaging member 7 to have the local rotation motion, at the respective shift pivoting positions P, Ps12S. The shift pivoting positions P, Ps12S adjoining to each other in the circumferential direction are positions for forming the overlap range Mo in which the circumferential direction shift ranges Mc of the local rotation motions at the respective shift pivoting positions overlap with each other.

This enables the CT scan, the panoramic exposure, and the cephalometric roentgenography with the X-ray imaging member 7 having a width of the light-receiving surface 7a in the predetermined direction which is smaller than the shift width Mw of the X-ray imaging member 7.

The imaging side drive unit 30 includes the interval adjusting mechanism 49 which can change the interval d1 between the rotation center line Lc and the light-receiving surface 7a, which makes it possible to change a photographing area on the light-receiving surface 7a without change of the shift pivoting quantity S by changing the interval d1 between the rotation center line Lc and the light-receiving surface 7a to enable the change in the photographing area on the light-receiving surface 7a. Accordingly, convenience of the X-ray photographing device 1 is enhanced.

The slit member 12 of the X-ray irradiating unit 10 includes the collimator 12c defining the irradiation range and the radiation direction of the X-ray beam 6 applied to the object 5. The collimator 12c shifts to trace the light-receiving surface 7a of the X-ray imaging member 7 having the local rotation motion to keep such a status that the collimator 12c, the object 5, and the light-receiving surface 7a are positioned on a line.

Because the collimator 12c moves to trace the light-receiving surface 7a while it is kept that the collimator 12c, the object 5, and the light-receiving surface 7a are positioned on the line, the X-ray beam 6 having the irradiation range and the irradiation direction defined by the collimator 12 can be accurately oriented to the object 5 and the light-receiving surface 7a, so that an accuracy in photographing can be increased.

Referring to FIGS. 5 to 12C, a modification of the first embodiment and a second embodiment and a modification thereof, third and fourth embodiments will be described. The second to fourth embodiments are partially different from the first embodiment and the remaining parts have basically the same configurations. Accordingly, descriptions of the same parts will be omitted or simplified and different points will be mainly described. In addition, the same member or corresponding members as those in the first embodiment are designated with the same references as required.

In addition, the second modification and their modifications have similar operations and advantageous effect as the first embodiment because of the same configuration as that of the first embodiment.

Figure 5:
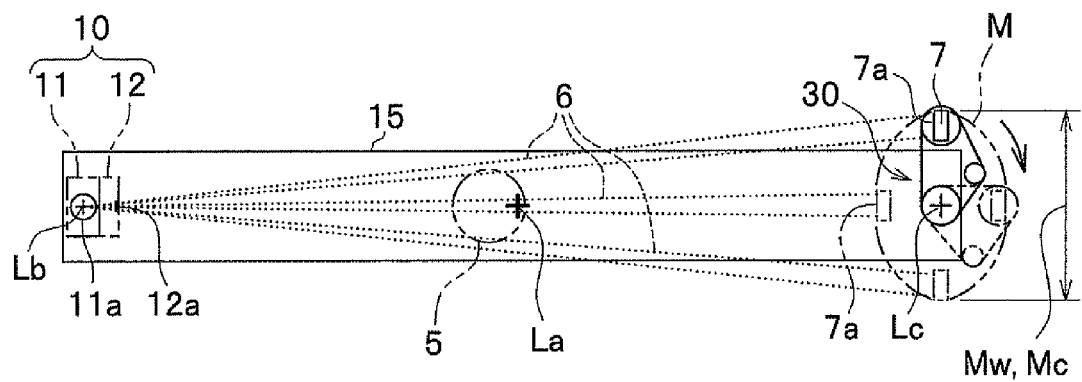
FIG. 5 shows a first modification of the first embodiment of the present invention, and corresponds to FIG. 3A.

Referring to FIGS. 2A, 2B, and 5, regarding the X-ray imaging member 7 of an X-ray photographing device 11 according to a first modification of the first embodiment, the servo motor 51 of the interval adjusting mechanism 49 is controlled by the control unit 60 to vary the interval d1 and the predetermined interval d2 by changing a length of the connecting member 43 in accordance with the position on the motion route M of the X-ray imaging member 7 caused by the local rotation motion. This causes the local rotation motion of the X-ray imaging member 7 to be a circular motion flatted in the radial direction with a center at the pivoting center line La or the irradiation direction. This flatted circular motion includes, for example, an oval motion or an ellipse motion. Here, the ellipse motion is, different from the oval motion, formed with a pair of substantially linear motions facing each other across the rotation center line Lc in the radial direction with the center at the pivoting center line La and substantially semi-circle motions continuous thereto facing each other across the center at the pivoting center line La in the circumferential direction.

Changing the interval d1 and the interval d2 in accordance with the position on the motion route M by the interval adjusting mechanism 49 makes it possible to set the motion route M in accordance with a shape of the object 5.

As described above, the interval adjusting mechanism 49 changes the interval d1 or the interval d2 in accordance with the position of the X-ray imaging member 7 on the motion route M, which makes it possible to differentiate, during the local motion or a pivoting motion of the X-ray imaging member 7, the interval d1 between the object 5 and the X-ray imaging member 7 or the predetermined interval d2 in accordance with the position of the X-ray imaging member 7 on the motion route M, which provides setting of the motion route M in accordance with the shape of the object 5, so that convenience in photographing can be enhanced.

In addition, making the local rotation motion of the X-ray imaging member 7 in the circle motion flattened in the irradiation direction can reduce a variation width of an enlargement/reduction ratio N for correcting the image data obtained from the X-ray imaging member 7, so that the photographing accuracy can be enhanced.

Figure 6:
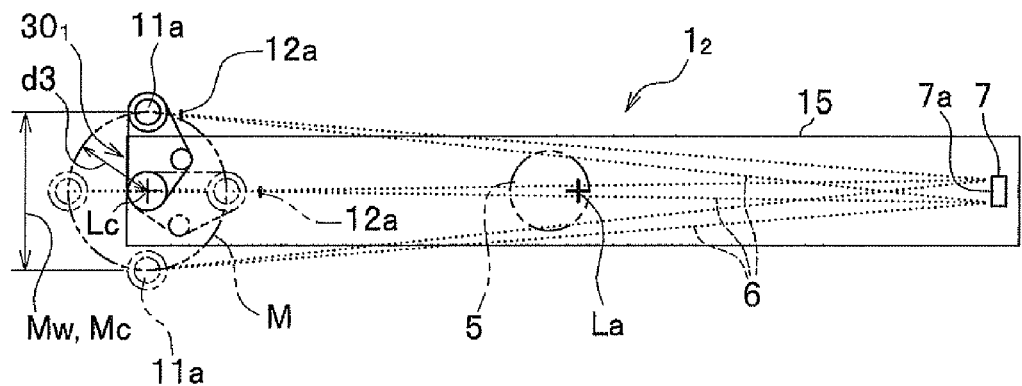
FIG. 6 shows a second modification of the first embodiment of the present invention and corresponds to FIG. 3A.

Referring to FIG. 6, an X-ray photographing device $1_2$ according to a second modification of the first embodiment includes an irradiation side drive unit $30_1$ in place of the imaging side drive unit 30 according to the first embodiment as the sub-drive unit. In the X-ray photographing device $1_2$, without the X-ray imaging member 7 performing the local rotation motion, the X-ray irradiating unit 10 (see FIG. 1) performs the local rotation motion as a driven member driven by the irradiation side drive unit $30_1$ having the same configuration as the imaging side drive unit 30 (see FIGS. 2A and 2B). Further, the drive unit 13 (see FIG. 1) driven by the irradiation side drive unit $30_1$ performs the local rotation motion together with the X-ray irradiating unit 10 and to cause the X-ray irradiating unit 10 to perform the rotation motion on the X-ray source 11a to shift the X-ray irradiating unit 10. In addition, in the second modification, similar to the first modification, an interval d3 between the rotation center line Lc and the X-ray source 11a can be changed in accordance with the position of the X-ray source 11a of the X-ray irradiating unit 10 on the motion route M by the interval adjusting mechanism (having the similar configuration to the interval adjusting mechanism 49) possessed by the irradiation side drive unit $30_1$.

Figure 7:
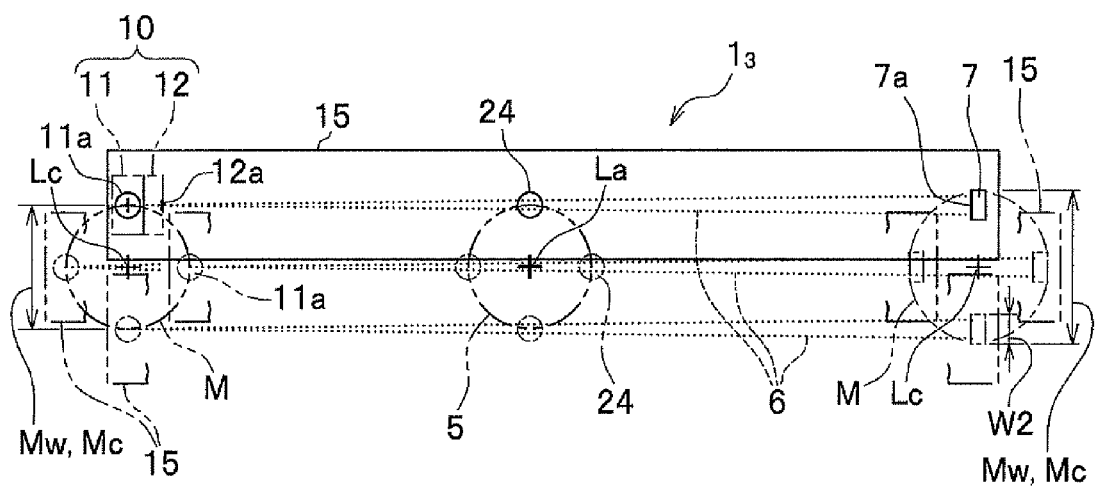
FIG. 7 shows a third modification of the first embodiment of the present invention and corresponds to FIG. 3A.

Referring to FIG. 7, in an X-ray photographing device $1_3$ according to the third modification of the first embodiment, the arm 15 performs the local rotation motion integral with the X-ray irradiating unit 10 and the X-ray imaging member 7 to cause the X-ray irradiating unit 10 and the X-ray imaging member 7 to perform the local rotation motion. The connecting shaft 24 during this operation performs the local rotation motion on the rotation center line Lc at the pivoting center line La. Accordingly, the X-ray photographing device $1_3$ is not provided with the imaging side drive unit 30 of the first embodiment and the irradiation side drive unit $30_1$ of the second modification, and the XY table 22 (see FIG. 1) controlled by the control unit 60 operates also as the sub-drive unit to cause the X-ray irradiating unit 10 and the X-ray imaging member 7 together with the arm 15 to have the local rotation motion.

In addition, the image processing unit 65 reconstructs the image data on the basis of the image data obtained by the local rotation motion of the X-ray irradiating member 10 and the X-ray imaging member 7 at a plurality of different shift pivot positions Ps to perform a reconstruction process to perform the image correction process.

According to the X-ray photographing device $1_3$ according to the third modification, the X-ray irradiating unit 10 and the X-ray imaging member 7 are caused to perform the local rotation motions using the XY table 22 which is a driving member forming the pivot drive unit 20. This eliminates use of the sub-drive unit specially provided to perform the local rotation motion, so that the configuration of the X-ray photographing device $1_3$ is simplified with cost reduction.

Referring to FIGS. 8A to 10, the second embodiment and modifications thereof will be described.

Figure 8A:
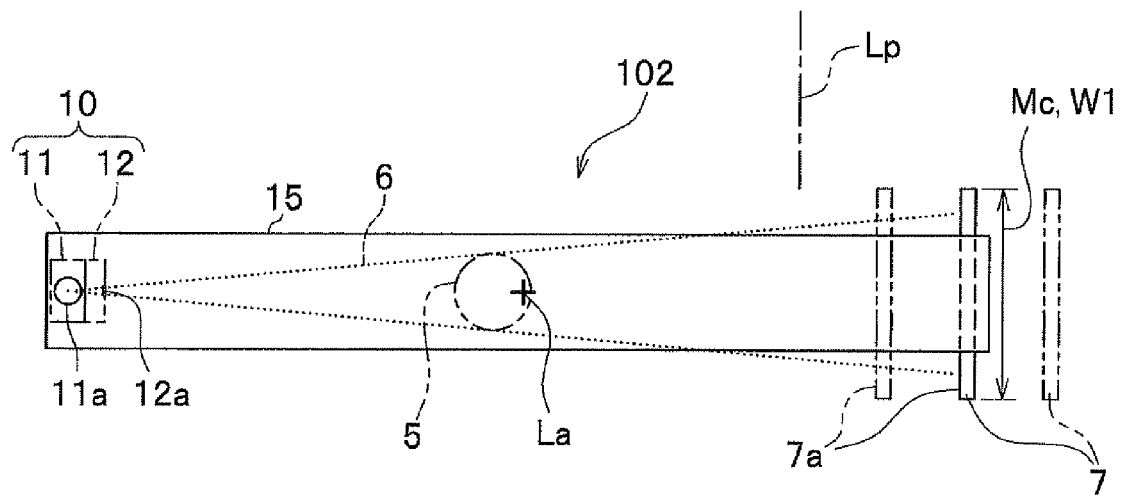
FIGS. 8A and 8B shows a second embodiment of the present invention, wherein FIG. 8A corresponds to FIG. 3A and FIG. 8B corresponds to FIG. 3B.

In X-ray photographing devices 102, $102_1$, $102_2$, the rotation center line Lc of the local rotation motion is substantially in parallel to a specific line Lp which is in parallel to an orthogonal line, i.e., a line orthogonal with the pivoting center line La, as an intersecting line intersecting the pivoting center line La (FIG. 8A shows, as an example, the specific line Lp which is substantially orthogonal with a plane including the pivoting center line La and the X-ray source 11a). Accordingly, regarding the local rotation motion, the light-receiving surface 7a rotates in a status in which the longitudinal direction of the light-receiving surface 7a is in parallel to the specific line Lp, i.e., the light-receiving surface 7a is slender in an orthogonal direction with the pivoting center line La.

In addition, in the X-ray photographing devices 102, $102_1$, $102_2$, the predetermined direction is a direction of the pivoting center line, and the shift width Mw of the local rotation motion is a width in the direction of the pivoting center line. The circumferential direction shift range Mc is a width in the circumferential direction of the light-receiving surface 7a, in this example, equal to the width W1 in the longitudinal direction.

Figure 8B:
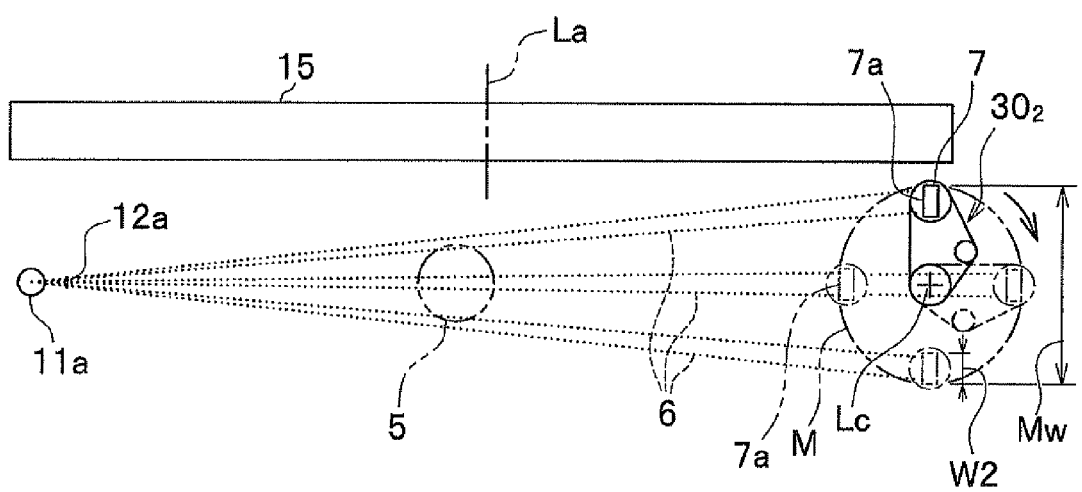

Referring to FIGS. 8A and 8B, the X-ray photographing device 102 according to the second embodiment corresponds to that of the first embodiment and includes, as a sub-drive unit, an imaging side drive unit $30_2$ having basically the same configuration as the imaging side drive unit 30 according to the first embodiment (see FIGS. 2A and 2B). The imaging side drive unit $30_2$ causes the X-ray imaging member 7 to have a local rotation motion on a center at the rotation center line Lc which is substantially in parallel to the specific line Lp which is substantially in parallel to the specific line Lp.

Figure 9:
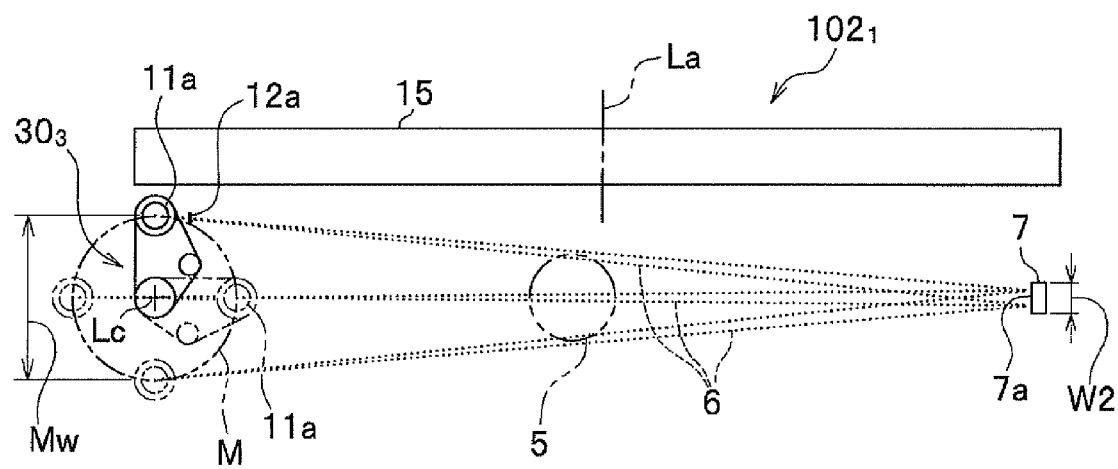
FIG. 9 shows a first modification of the second embodiment of the present invention and corresponds to FIG. 6.

In addition, the X-ray photographing device $102_1$ of a first modification of the second embodiment shown in FIG. 9 corresponds to the X-ray photographing device $1_2$ of the second modification of the first embodiment and includes imaging side drive unit $30_3$, as sub-drive unit, substantially the same configuration as the irradiation side drive unit $30_1$ (see FIG. 6). The X-ray imaging member 7 performs a local rotation motion on the rotation center line Lc which is substantially in parallel to the specific line Lp (see FIG. 8A).

Figure 10:
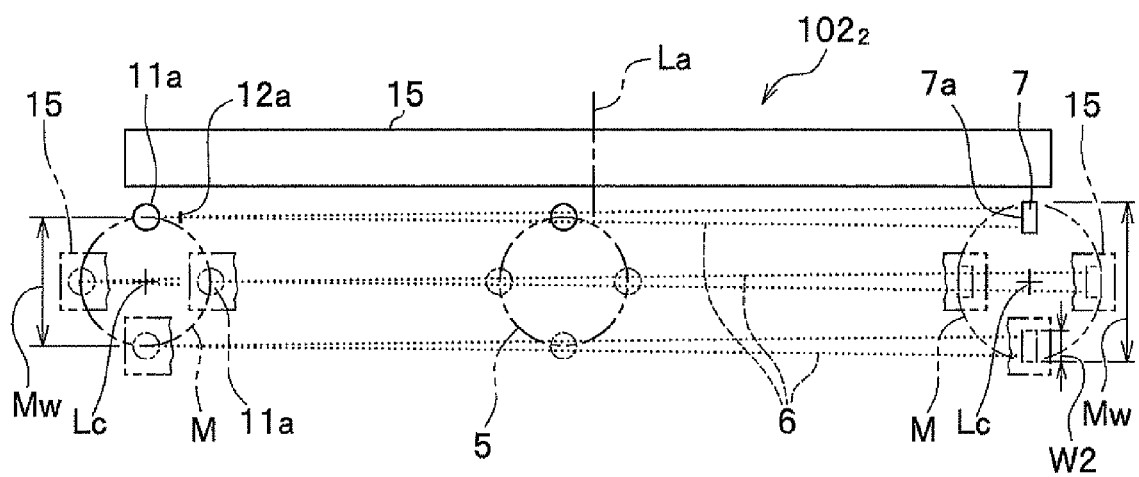
FIG. 10 shows a second modification of the second embodiment of the present invention and corresponds to FIG. 7.

In addition, the X-ray photographing device $102_2$, shown in FIG. 10, of a second modification of the second embodiment corresponds to the X-ray photographing device $1_3$ of the third modification of the first embodiment and includes, as a sub-drive unit, a two-dimensional drive unit (not shown) for moving the arm 15 using, as a two-dimensional plane, a plane in parallel to the pivoting center line La, i.e., a vertical plane, in addition to the XY table 22 (FIG. 1) or in place of the XY table 22.

According to the second embodiment and the first and second modifications of the second embodiment, the rotation center line Lc is substantially in parallel to the specific line Lp (see FIG. 8A) which is in parallel to an orthogonal line to the pivoting center line La. The predetermined direction is a direction substantially in parallel to the pivoting center line La.

This enables the X-ray photographing with a large image range in the direction of the pivoting center line by using the X-ray imaging member 7 of a low cost because the X-ray imaging member 7 has the light-receiving surface 7a with the width W2 smaller than the shift width Mw of a X-ray imaging member 7 in the pivoting center line though a low-cost X-ray imaging member 7 is used.

Referring to FIGS. 11A to 12C, in the X-ray photographing devices 103, 104 according to the third and fourth embodiments, the X-ray imaging member 7 performs the local rotation motion on the rotation center line Lc which is in parallel to the orthogonal line (line orthogonally intersecting the pivoting center line La) as a line intersecting the pivoting center line La and on one plane intersecting (here substantially orthogonally intersecting) the rotation center line Lc.

Figure 11A:
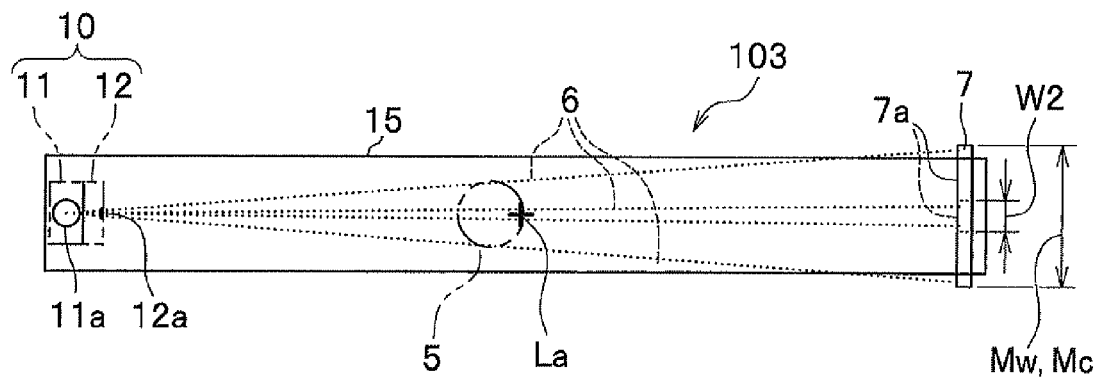
FIGS. 11A to 11C show a third embodiment of the present invention, wherein FIG. 11A corresponds to FIG. 3A, FIG. 11B corresponds to FIG. 3B.
Figure 11B:
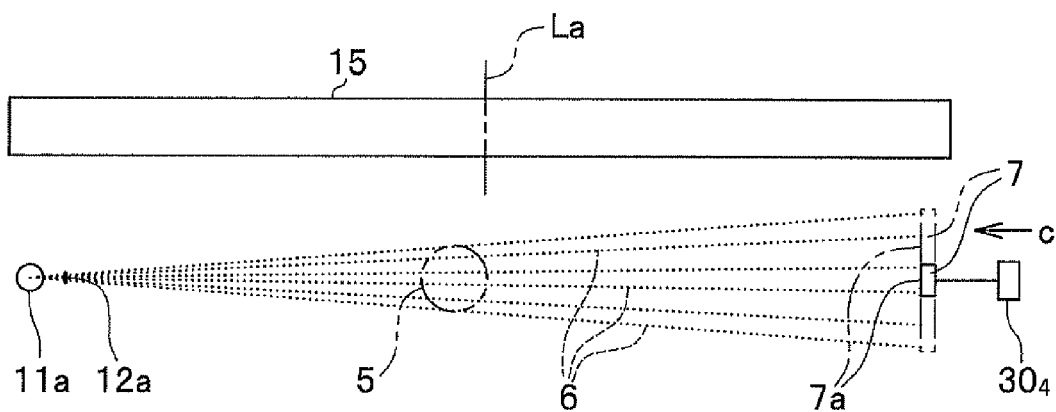
Figure 11C:
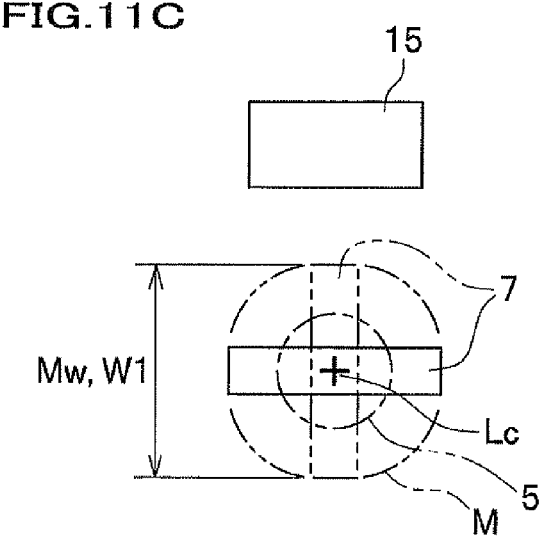

Referring to FIGS. 11A to 11C, in the X-ray photographing device 103 of the third embodiment, the local rotation motion is performed on the rotation center line Lc intersecting the pivoting center line La and the light-receiving surface 7a. In addition the light-receiving surface 7a of the X-ray imaging member 7 performing the local rotation motion by being driven by an image side drive unit $30_4$ as a sub-drive unit rotates substantially in parallel to a plane orthogonal with the rotation center line Lc. The predetermined direction is a circumferential direction regarding a center at the pivoting center line La.

In addition, the drive unit 13 (see FIG. 1) causes the slit member 12 to perform a rotation motion on a center at the X-ray source 11a in synchronism with the local rotation motion so that the X-ray beam 6 having a slit shape tracks the light-receiving surface 7a performing the local rotation motion.

Figure 12A:
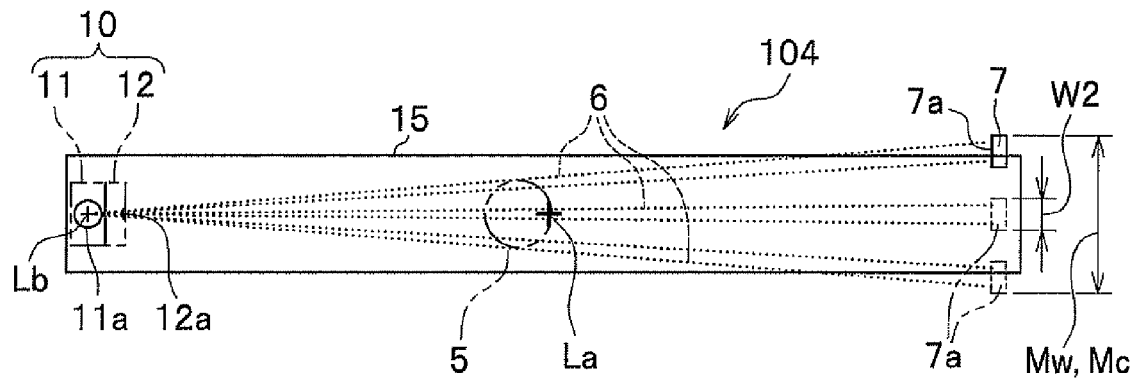
FIGS. 12A to 12C show a fourth embodiment of the present invention, wherein FIG. 12A corresponds to FIG. 3A, FIG. 12B corresponds to FIG. 3B.
Figure 12B:
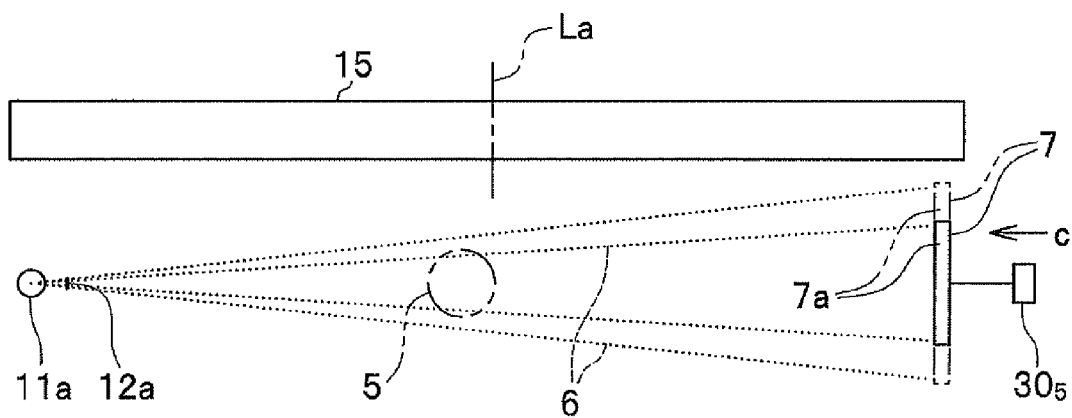
Figure 12C:
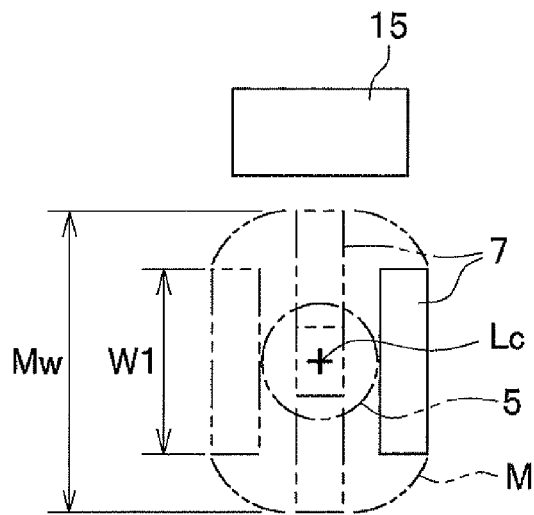

Referring to FIGS. 12A to 12C, the X-ray photographing device 104 according to the fourth embodiment includes, as a sub-drive unit, an imaging side drive unit $30_5$ having substantially the same configuration as the imaging side drive unit 30. The light-receiving surface 7a of the X-ray imaging member 7 performing the local rotation motion by being driven by the imaging side drive unit $30_5$ rotates in such a state that the longitudinal direction of the light-receiving surface 7a is substantially in parallel to the pivoting center line La during the local rotation motion, i.e., such a state as to be slender in an orthogonal direction with the direction of the pivoting center line. The predetermined direction is a circumferential direction regarding a center at the pivoting center line La.

In addition, the drive unit 13 (see FIG. 1) causes the slit member 12 to perform a rotary motion on the X-ray source 11a so that the X-ray beam 6 having the slit shape traces the light-receiving surface 7a having the local rotation motion.

In addition, as a modification of the fourth embodiment, the light-receiving surface 7a may be one rotating in such a state that the longitudinal direction of the light-receiving surface 7a is substantially in parallel to the specific line Lp (see FIG. 8A), i.e., such a state as to be slender in an orthogonal direction with the direction of the pivoting center line.

Hereinbelow an embodiment having a partially modified configuration of the above embodiments will be described regarding the modified configuration.

Photographing timing with the X-ray photographing device may be when a pivoting angle due to the pivoting motion of the arm 15 is equal to or less than 180 degrees.

The rotation center line Lc may be arranged such that in a case where the driven member makes one revolution on the center at the Lc, the object 5 is positioned only in a limited region less than one revolution between an X-ray irradiating unit 10 and the X-ray imaging member 7.

In the second to fourth embodiments and their modifications, the intersecting line intersecting the pivoting center line La may intersect the pivoting center line La in a manner other than orthogonal intersecting.

The supporting member for supporting the X-ray irradiating unit 10 and the X-ray imaging member 7 may be configured as separate supporting members for respectively supporting the X-ray irradiating unit 10 and the X-ray imaging member 7. In addition, in that case, the pivoting center line La may be provided separately from the X-ray irradiating unit 10 and the X-ray imaging member 7.

The X-ray photographing devices are usable for other medical practice other than the dental practice. In addition the object may be substances other than the human being. Accordingly, the X-ray photographing device may be used for inspection of substances.

DESCRIPTION OF REFERENCE SYMBOL 1, 102, 103, 104 X-ray photographing device
5 object
6 X-ray beam
7 X-ray imaging member
7a light-receiving surface
10 X-ray irradiating unit
20 pivot drive unit
22 XY table
30, $30_2$, $30_4$, $30_5$ imaging side drive unit
$30_1$, $30_3$ irradiation side drive unit
60 control unit
La pivoting center line
Lc rotation center line
M motion route
Mw shift width
Ps shift pivot position
S shift pivoting quantity
Mc circumferential direction shift range
Mc overlap range

The invention claimed is:

1. An X-ray photographing device comprising: an X-ray irradiating unit configured to irradiate an object with an X-ray beam; an X-ray imaging member having a light-receiving surface configured to receive the X-ray beam transmitted through the object; a pivot drive unit configured to cause the X-ray irradiating unit and the X-ray imaging member to have a pivoting motion on a pivoting center line around the object; and a control unit configured to control the pivot drive unit, the X-ray photographing device further comprising a sub-drive unit, controlled by the control unit, configured to cause a driven member which is at least one of the X-ray irradiating unit and the X-ray imaging member to a local motion which is different from the pivoting motion with a shift width in a predetermined direction, wherein
a width of the light-receiving surface in the predetermined direction is smaller than the shift width, and wherein
the local motion is a motion made on the rotation center line.

2. The X-ray photographing device as claimed in claim 1, wherein the rotation center line is arranged such that the object is always positioned between the X-ray irradiating unit and the X-ray imaging member when one revolution of the driven member is made on the rotation center line.

3. The X-ray photographing device as claimed in claim 1, wherein
the pivot drive unit causes the X-ray irradiating unit and the X-ray imaging member to perform shift pivoting motions, each having a shift pivoting quantity smaller than one revolution of the pivoting motion to locate the X-ray irradiating unit and the X-ray imaging member at a shift pivot position, and wherein
the sub-drive unit causes the driven member to perform the local rotation motion at each of the shift pivot positions, and the shift pivot positions adjoining to each other in the circumferential direction are positions allowing formation of an overlap range between the circumferential direction shift ranges of the local rotation motion in the circumferential direction.

4. The X-ray photographing device as claimed in claim 1, wherein the rotation center line is substantially in parallel to a line in parallel to an orthogonal line orthogonal with the pivoting center line, and the predetermined direction is a direction in parallel to the pivoting center line.

5. The X-ray photographing device as claimed in claim 1, wherein the sub-drive unit includes an interval adjusting mechanism capable of changing an interval between the rotation center line and the driven member.

6. The X-ray photographing device as claimed in claim 5, wherein the interval adjusting mechanism changes the interval in accordance with a position of the driven member on a motion route of the local rotation motion.

7. The X-ray photographing device as claimed in claim 1, wherein the driven member is the X-ray imaging member, and the X-ray irradiating unit includes a collimator defining an irradiation range and an irradiation direction of the X-ray beam applied to the object, and wherein the collimator moves to track the X-ray imaging member to keep a status in which the collimator, the object, and the light-receiving surface are positioned on a line.

* * * * *